(12) United States Patent
Fujita et al.

(10) Patent No.: US 7,781,711 B2
(45) Date of Patent: Aug. 24, 2010

(54) FLUORESCENCE MICROSCOPE FOR WHICH A SAMPLE IS OBSERVED BASED ON THE SATURATION COMPONENTS OF FLUORESCENCE AND FLUORESCENCE MICROSCOPY METHOD

(75) Inventors: Katsumasa Fujita, Osaka (JP); Satoshi Kawata, Osaka (JP); Osamu Nakamura, Osaka (JP); Naoko Nakamura, legal representative, Osaka (JP); Minoru Kobayashi, Osaka (JP)

(73) Assignee: Osaka University, Suita-shi, Osaka (JP)

( * ) Notice: Subject to any disclaimer, the term of this patent is extended or adjusted under 35 U.S.C. 154(b) by 373 days.

(21) Appl. No.: 11/792,304

(22) PCT Filed: Oct. 14, 2005

(86) PCT No.: PCT/JP2005/018945
§ 371 (c)(1),
(2), (4) Date: Mar. 12, 2008

(87) PCT Pub. No.: WO2006/061947
PCT Pub. Date: Jun. 15, 2006

(65) Prior Publication Data
US 2008/0215272 A1 Sep. 4, 2008

(30) Foreign Application Priority Data
Dec. 8, 2004 (JP) ............................. 2004-355483

(51) Int. Cl.
*G02B 7/04* (2006.01)
(52) U.S. Cl. .................................... 250/201.3; 250/234
(58) Field of Classification Search .............. 250/201.3, 250/234, 235, 306–311, 461.1, 461.2, 458.1, 250/459.1
See application file for complete search history.

(56) References Cited

U.S. PATENT DOCUMENTS 5,233,197 A * 8/1993 Bowman et al. ......... 250/461.1
5,294,799 A 3/1994 Aslund et al.

FOREIGN PATENT DOCUMENTS

GB 2 231 958 A 11/1990

OTHER PUBLICATIONS

"Saturated patterned excitation microscopy—a concept for optical resolution improvement", Rainer Heintzmann, Thomas M. Jovin, and Christoph Cremer, Josa A, vol. 19, Issue 8, pp. 1599-1609 (2002) doi:10.1364/JOSAA.19.001599.
European Search Report dated Jun. 21, 2010.

* cited by examiner

*Primary Examiner*—Que T Le
(74) *Attorney, Agent, or Firm*—McGinn IP Law Group, PLLC

(57) ABSTRACT

To increase spatial resolution by observing a sample based on saturated fluorescence components. A fluorescence microscope according to the present invention includes: a laser light source 10 emitting laser light as excitation light; an objective lens 13 focusing the laser light and applying the focused laser light to a sample 14; a detector 22 detecting fluorescence generated in the sample 14 with the laser light; and a stage 15 scanning the sample 14 while moving the sample 14 relative to the laser light, wherein the laser light is applied to the sample with varying intensities such that saturation of fluorescence occurs at the maximum intensity of the laser light, and fluorescence is detected with the detector in accordance with intensity of the laser light, and the sample is observed based on the saturation components of fluorescence.

19 Claims, 5 Drawing Sheets

FLUORESCENCE MICROSCOPE FOR WHICH A SAMPLE IS OBSERVED BASED ON THE SATURATION COMPONENTS OF FLUORESCENCE AND FLUORESCENCE MICROSCOPY METHOD

TECHNICAL FIELD

The present invention relates to a fluorescence microscope and a fluorescence microscopy method. In particular, the invention relates to a fluorescence microscope and a fluorescence microscopy method, which irradiate a sample with excitation light and detects fluorescence emitted by the sample to observe the sample.

BACKGROUND ART

Nowadays, fluorescence microscopes have been widely used as a tool efficient for medical and biological researches. In the fluorescence microscopes, excitation light from a light source is applied to a fluorescent material in a sample to make the fluorescent material emit fluorescence. Then, the fluorescence separated from the excitation light is detected to observe a fluorescence image of the sample. In the fluorescence microscopes, a fluorescent material is used as a fluorescence probe to label various cells or proteins and observe localization thereof.

Further, a laser-scanning type fluorescence microscope has been used (for example, see Patent Documents 1 and 2). The laser-scanning type fluorescence microscope scans and irradiates a sample with laser light to capture a fluorescence image thereof.

A spatial resolution of a general microscope is limited by diffraction limit. Thus, existing microscopes have a problem that once a light wavelength and a numeric aperture are determined, the spatial resolution cannot be increased beyond a certain level.

[Patent Document 1]

Japanese Unexamined Patent Application Publication No. 2003-057554

[Patent Document 2]

Japanese Unexamined Patent Application Publication No. 2003-344776

DISCLOSURE OF THE INVENTION

Problems to be Solved by the Invention

As described above, the existing microscopes have a problem that spatial resolution cannot be increased.

The present invention has been accomplished in view of the above problems, and an object of the invention is to provide fluorescence microscope and a fluorescence microscopy method, which can increase spatial resolution.

Means for solving the problems

According to a first aspect of the present invention, a fluorescence microscope includes: a laser light (for example, a light source 10 of an embodiment of the present invention) source emitting laser light as excitation light; an objective lens (for example, an objective lens 13 of an embodiment of the present invention) focusing the laser light and applying the focused laser light to a sample; a detector (for example, a detector 22 of an embodiment of the present invention) detecting fluorescence generated in the sample with the laser light; and a scanning unit (for example, a stage 15 of an embodiment of the present invention) scanning the sample while moving the sample relative to the laser light, wherein the laser light is applied to the sample with varying intensities to be in a nonlinear range at a maximum intensity, a saturation of fluorescence occurring in the nonlinear range such that an intensity of the laser light and an intensity of fluorescence have a nonlinear relation, and the fluorescence corresponding the intensity of the laser light is detected with the detector, and the sample is observed based on the saturation components of fluorescence. Hence, spatial resolution can be increased.

According to a second aspect of the present invention, the fluorescence microscope further includes: a modulator (for example, a modulator 16 of an embodiment of the present invention) modulating intensity of the laser light such that the intensity is changed with time wherein the sample is irradiated with intensity to be in the nonlinear range at a time when the intensity of the laser light peaks; the sample is scanned under modulation with the modulator, and fluorescence generated in the sample is detected with the detector; and harmonic components are extracted from the fluorescence detected with the detector. Hence, spatial resolution can be increased with simple structure.

According to a third aspect of the present invention, in the fluorescence microscope, the harmonic components are extracted with a lock-in amplifier. Thus, high-sensitivity detection can be performed.

According to a fourth aspect of the present invention, in the fluorescence microscope, the laser light source is a pulse laser light source. Thus, it is possible to prevent the sample from being damage or the fluorescence from being faded.

According to a fifth aspect of the present invention, in the fluorescence microscope, the laser light is applied to the sample at least two intensities of a first intensity being in the nonlinear range and a second intensity different from the first intensity, and scanning is perform under such a condition that the laser light is applied to the sample with each of the first and second intensity, and the saturation components of fluorescence from the sample are derived based on fluorescence intensity at the first intensity and fluorescence intensity at the second intensity.

According to a sixth aspect of the present invention, in the fluorescence microscope, the laser light source is a multiphoton excitation light source generating multiphoton excitation. Hence, higher-sensitivity detection can be performed.

According to a seventh aspect of the present invention, the fluorescence microscope further includes: a separating unit separating fluorescence from the laser light based on a wavelength difference, wherein the fluorescence separated with the separating unit is detected with the detector. Hence, spatial resolution can be increased with simple structure.

According to an eighth aspect of the present invention, the fluorescence microscope further includes: a focus position changing unit changing a focus position of the objective lens along an optical axis. Hence, three-dimensional observation of the sample becomes possible.

According to a ninth aspect of the present invention, in the fluorescence microscope, the fluorescence generated by applying the laser light to the sample is detected with the detector through a confocal optical system. Hence, spatial resolution can be more increased.

According to a tenth aspect of the present invention, a fluorescence microscopy method for irradiating a sample with laser light as excitation light to detect fluorescence from the sample to observe the sample, includes: focusing the laser light and applying the focused laser light to a sample; changing intensity of the laser light to be in a nonlinear range at a maximum intensity, saturation of fluorescence occurring in the nonlinear range such that the intensity of the laser light and intensity of fluorescence have a nonlinear relation; separating the laser light and fluorescence generated in the sample and derived from the laser light; detecting the fluorescence separated from the laser light; and observing the sample based on saturation components of fluorescence with the detected fluorescence. Hence, spatial resolution can be increased.

According to an eleventh aspect of the present invention, the fluorescence microscopy method further includes: modulating intensity of the laser light such that the intensity is changed with time; focusing laser light and applying the laser light to the sample to be in the nonlinear range at a time when the modulated laser light peaks; and moving the sample relative to the laser light under modulation with the modulator. Hence, spatial resolution can be increased with a simple method.

According to a twelfth aspect of the present invention, in the fluorescence microscopy method, harmonic components corresponding to a modulation frequency are extracted from the detected fluorescence to observed. Hence, spatial resolution can be easily increased.

According to a thirteenth aspect of the present invention, in the fluorescence microscopy method, the laser light is a pulse laser light, and the pulse laser light is intensity-modulated. Hence, higher-sensitivity detection can be performed. Hence, higher-sensitivity detection can be performed.

According to a fourteenth aspect of the present invention, in the fluorescence microscopy method, the laser light is applied to the sample at least two intensities of a first intensity being in the nonlinear range and a second intensity different from the first intensity, and scanning is perform with each of the first and second intensity; and saturation components of fluorescence are derived based on fluorescence intensity at the first intensity and fluorescence intensity at the second intensity. Hence, spatial resolution can be increased with a simple method.

According to a fifteenth aspect of the present invention, in the fluorescence microscopy method, fluorescence is detected by a multiphoton excitation method. Hence, higher-sensitivity detection can be performed.

According to a sixteenth aspect of the present invention, in the fluorescence microscopy method, the sample is labeled with a quantum dot. Hence, it is possible to use low intensity laser light.

According to a seventeenth aspect of the present invention, in the fluorescence microscopy method, a focus position of the laser light in the sample changes along an optical axis to detect the fluorescence. Hence, three-dimensional observation of the sample becomes possible.

According to a eighteenth aspect of the present invention, in the fluorescence microscopy method, the fluorescence generated by applying the laser light to the sample is detected through a confocal optical system. Hence, spatial resolution can be more increased.

According to a nineteenth aspect of the present invention, a fluorescence microscope includes: a laser light source emitting laser light as excitation light; an objective lens focusing the laser light and applying the focused laser light to a sample; a detector detecting fluorescence generated in the sample with the laser light; and a scanning unit scanning the sample while moving the sample relative to the laser light, wherein the laser light is applied to the sample with varying intensities such that saturation of fluorescence occurs at a maximum intensity of the laser light, and the fluorescence corresponding to the intensity of the laser light is detected with the detector, and the sample is observed based on saturation components of fluorescence. Hence, spatial resolution can be more increased.

Incidentally, in the above microscopy method, the order of steps is not limited to the above order unless otherwise specified.

ADVANTAGES OF THE INVENTION

According to the present invention, it is possible to provide a fluorescence microscope and a fluorescence microscopy method, which realize high spatial resolution.

DESCRIPTION OF REFERENCE NUMERALS

Figure 1:
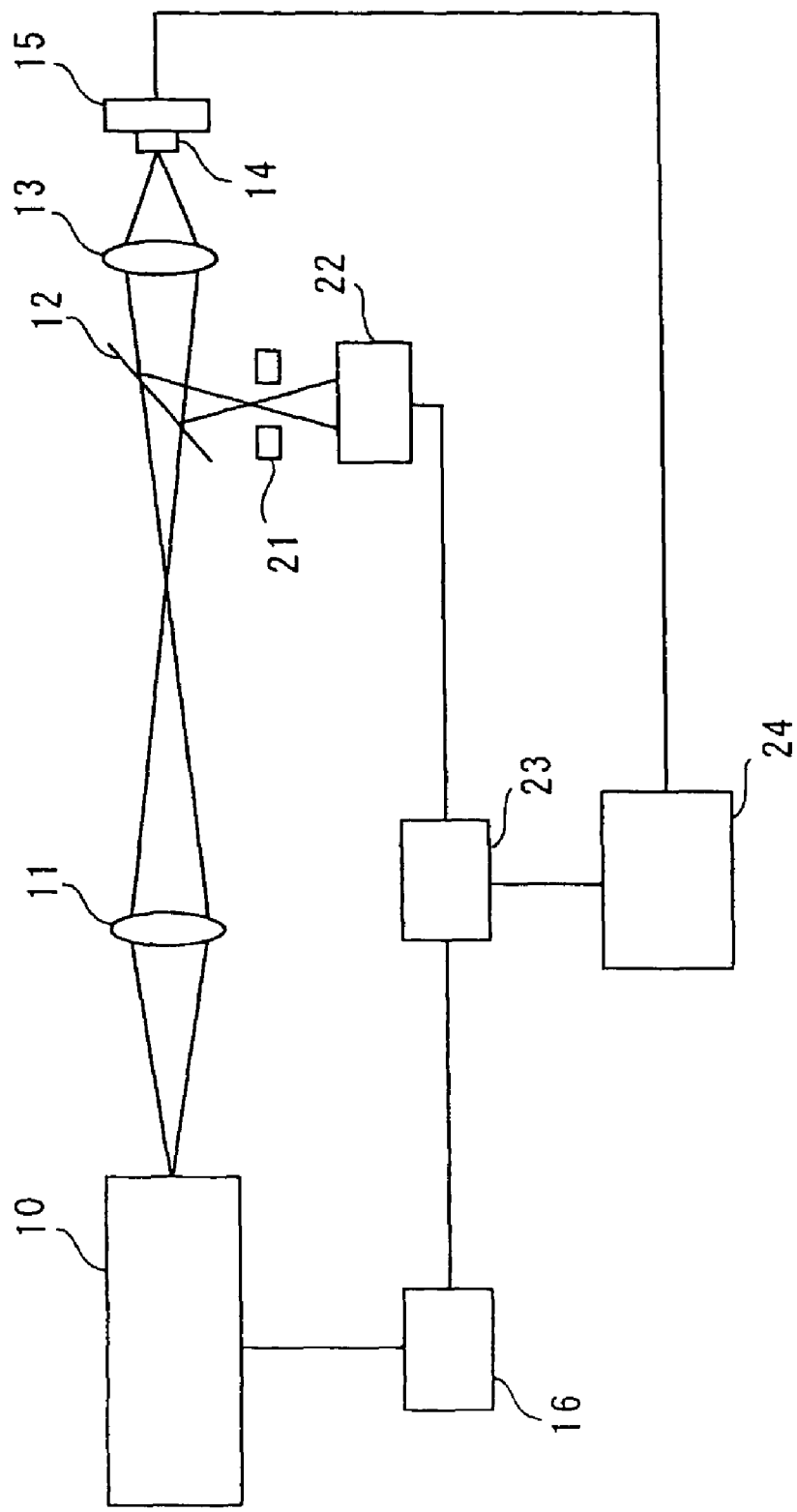
FIG. 1 shows the structure of a fluorescence microscope according to the present invention.

10 light source
11 lens
12 dichroic mirror
13 objective lens
14 sample
15 stage
16 modulator
21 pinhole
22 detector
23 lock-in amplifier
24 processing apparatus

BEST MODES FOR CARRYING OUT THE INVENTION

Hereinafter, embodiments of the present invention are described. The following description is directed to the embodiments of the present invention for illustrative purpose only, and the present invention should not be construed as limited to the following embodiments. Components etc. in the following description are omitted or simplified as appropriate for clear explanation. Those skilled in the art would easily understand that components can be changed, added, or exchanged in the following embodiments within the scope of the present invention. The same components are denoted by identical reference numerals throughout the drawings, and description thereof is omitted if not necessary.

First Embodiment

A fluorescence microscope according to a first embodiment of the present invention is a confocal microscope, in other words, a laser scanning type microscope. According to the present invention, spatial resolution is increased by utilizing saturation of fluorescence. That is, saturated components of fluorescence are observed to improve the spatial resolution. Referring to FIG. 1, the fluorescence microscope is described below. FIG. 1 schematically shows the structure of a fluorescence microscope of the present invention. Referring numeral 10 denotes a light source; 11, a lens; 12, a dichroic mirror; 13, a objective lens; 14, a sample; 15, a stage; 16, a modulator; 21, a pinhole; 22, a detector; 23, a lock-in amplifier; and 24, a processing apparatus.

The light source 10 is a laser light source for continuously emitting excitation light; for example, a continuous-wave Ar ion laser or a semiconductor ion laser having a wavelength in a visible range can be used. Here, the light source 10 has a wavelength enough to excite a fluorescent material. Laser light as the excitation light is intensity-modulated with the modulator 16, and takes aperiodic function with a frequency f. In this example, the laser light is modulated such that its intensity takes a cosine function. That is, provided that $\omega$ ($=2\pi f$) represents an angular frequency in intensity modulation and t represents time, excitation light intensity is proportional to $1+\cos(\omega t)$. The intensity-modulated excitation light takes the maximum intensity value at $\omega t = 2n\pi$ and the minimum intensity value at $\omega t = (2n+1)\pi$ (n is an arbitrary natural number). Incidentally, an initial phase is set to 0. In this example, light is modulated with f=100 kHz, for example. As the modulator 16, an electro-optical modulator or an acousto-optical modulator can be used.

The modulated excitation light is refracted by the lens 11 and then enters the dichroic mirror 12. The dichroic mirror 12 reflects only light of a particular wavelength range, and transmits light of the other wavelength range. In this example, the mirror transmits laser light, and reflects fluorescence from the sample 14. As a result, the excitation light and the fluorescence are separated in accordance with a wavelength difference. In general, fluorescence has a wavelength longer than that of excitation light due to Stokes shift. Thus, the excitation light and the fluorescence can be efficiently separated by using the dichroic mirror 12. Needless to say, optical separation means other than the dichroic mirror may be used to separate the fluorescence from the excitation light. For example, a filter and a beam splitter may be used in combination to separate the fluorescence from the excitation light.

The excitation light transmitted through the dichroic mirror 12 enters the objective lens 13. The objective lens 13 concentrates the excitation light so as to form an image on or in the sample, and the concentrated light enters the sample 14. As the sample 14, a biological sample stained with, for example, an immunostaining method can be used. After the excitation light is incident, fluorescence is generated based on the excitation light. Here, intensity of the fluorescence is determined by intensity of the excitation light. The fluorescence is refracted by the objective lens 13 and incident on the dichroic mirror 12. As described above, since the dichroic mirror 12 reflects light in accordance with a wavelength, the mirror transmits the laser light reflected by the sample 14 and reflects the fluorescence. In this way, the excitation light reflected by the sample 14 can be separated from the fluorescence.

The fluorescence reflected by the dichroic mirror 12 passes through the pinhole 21 and enters the detector 22. Incidentally, the fluorescence is refracted by the objective lens 13 to focus on the pinhole 21. The fluorescence incident on the detector 22 is based on the modulated excitation light. The detector 22 is a point sensor such as a photoelectron multiplier. The detector 22 sends a detection signal to the lock-in amplifier 23 in accordance with intensity of the received light. The lock-in amplifier 23 locks in a predetermined repetition frequency, and lock-in detects a signal from the detector 22. Here, the lock-in amplifier 23 receives a reference signal from the modulator 16, and detects a signal with a frequency n times (n is an integer of 2 or more) hither than a modulation frequency fin the modulator 16. For example, assuming that the modulation frequency is 100 kHz, a signal is detected with a repetition frequency of 200 kHz, 300 kHz, . . . . As a result, high-order frequency components can be extracted and detected.

The stage 15 is an XYZ stage with a driving mechanism. The stage is movable in a 3D space. That is, the stage 15 is movable in a horizontal direction (XY-direction) and a vertical direction (Z direction). The fluorescence is detected while the stage 15 is moved. For example, the stage 15 is moved at constant speed while the sample 14 is irradiated with laser light to thereby move the sample 14 relative to the excitation light. Then, the entire surface of the sample 14 is scanned with light. The processing apparatus 24 is, for example, a personal computer and controls movement of the stage 15. For example, the stage 15 is moved in the X direction to scan the sample 14 from end to end. Then, the stage is shifted in the Y direction to continue scanning the sample in the X direction. This operation is repeated. After the completion of scanning one plane in the sample 14, the stage is moved in the Z direction, and the sample is scanned similarly in the XY-direction. That is, the stage 15 is moved in the Z-direction to dislocate the focus position in an optical axis direction. Therefore, the focus position in the sample is moving along the optical axis and three-dimensional observation of the sample becomes possible. As described above, changing a distance between the objective lens 13 and stage 15 by driving the stage 15 enable to change the focus position along the optical axis. Needless to say, it is possible to move the objective lens 13 instead of the stage 15. That is, it becomes possible to change the focus position along the optical axis by increasing or decreasing the distance between the objective lens 13 and the stage 15. This scanning operation is repeated to three-dimensionally scan all or part of the sample 14. Furthermore, scanning in the XY direction is not limited to a way using stage 15. It is possible to use a beam deflection apparatus such as a galvano-mirror or an acousto-optics element to scan in XY-direction.

Further, the processing apparatus 24 controls the stage 15 and the lock-in amplifier 23 to perform lock-in detection during the scanning operation of the sample 14. In addition, the processing apparatus 24 forms a fluorescence image in accordance with a signal output from the lock-in amplifier. The fluorescence image is formed based on the signal detected during the scanning operation of the sample 14. The fluorescence image can be displayed on a screen or data about the fluorescence image can be stored by the processing apparatus 24 executing predetermined operations. As a result, an image can be observed or captured.

The fluorescence microscope of this embodiment configures a confocal microscope. That is, the components are arranged such that the light source 10 as a point light source is in optically conjugate relationship with the sample 14, and the sample 14 is in optically conjugate relationship with the pinhole 21. Thus, the fluorescence can be detected through a confocal optical system. Hence, the spatial resolution can be increased.

Figure 2:
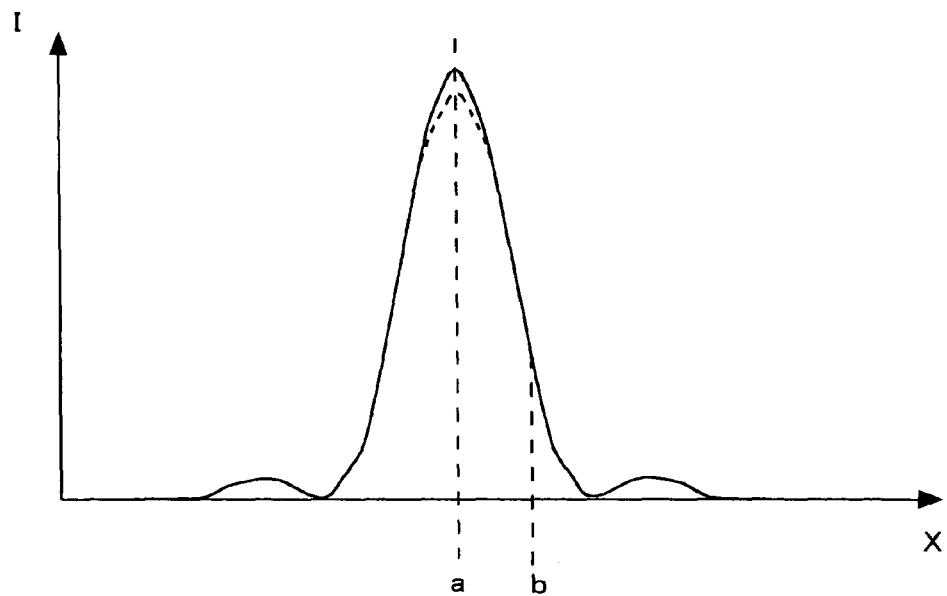
FIG. 2 schematically shows spatial distribution of laser light as excitation light and fluorescence derived from the excitation light.
Figure 3A:
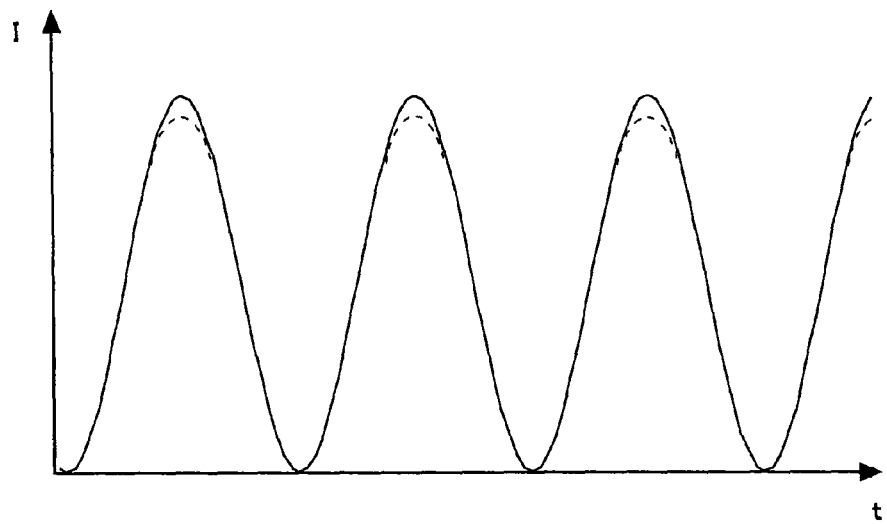
FIG. 3A schematically shows an intensity change of excitation light modulated with a fluorescence microscope according to a first embodiment of the present invention and fluorescence derived from the excitation light.
Figure 3B:
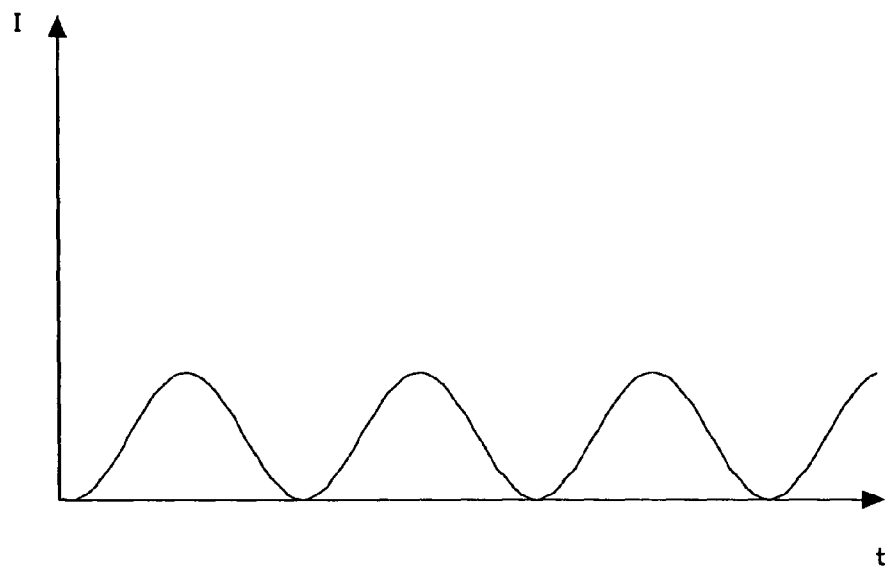
FIG. 3B schematically shows an intensity change of excitation light modulated with the fluorescence microscope according to the first embodiment of the present invention and fluorescence derived from the excitation light.
Figure 4:
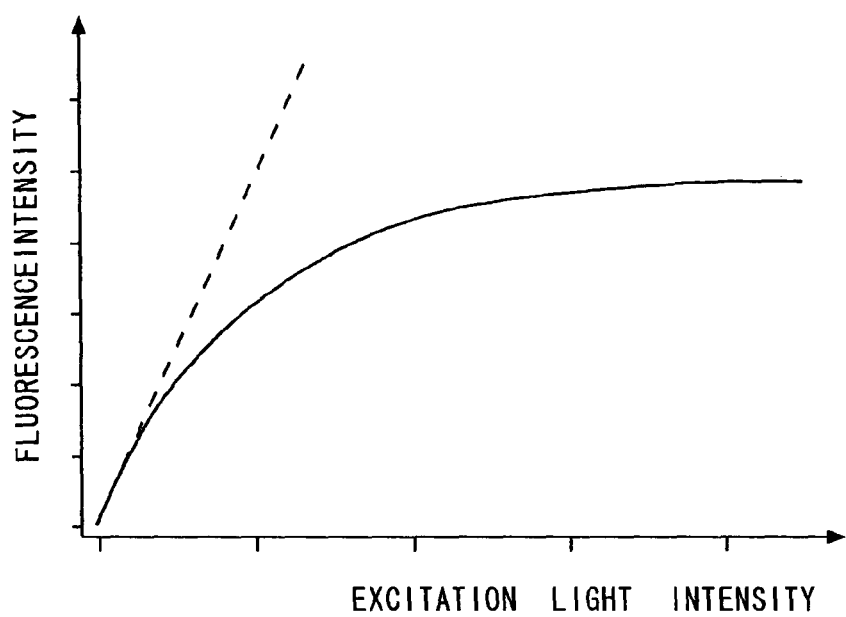
FIG. 4 schematically shows a relation between excitation light intensity and fluorescence intensity.

Referring to FIGS. 2 to 4, the principle of high-resolution detection based on saturation of the fluorescence is described next. FIG. 2 shows spatial distribution of intensity of laser light (excitation light) and fluorescence. In FIG. 2, the horizontal axis represents a position, and the vertical axis represents light intensity. FIGS. 3A and 3B show a change with time of intensity of modulated laser light (excitation light) and fluorescence. In FIGS. 3A and 3B, the horizontal axis represents time, and the vertical axis represents light intensity. Further, in FIG. 2 and FIGS. 3A and 3B, the solid line represents excitation light intensity, and the broken line represents fluorescence intensity. For ease of explanation, in FIG. 2 and FIGS. 3A and 3B, intensity of the excitation light corresponds to intensity of the fluorescence with the fluorescence unsaturated. FIG. 4 shows a relationship between excitation light intensity and fluorescence intensity. In FIG. 4, the horizontal axis represents excitation light intensity, and the vertical axis represents fluorescence intensity.

As shown in FIG. 2, the intensity of laser light reaches its peak value at the center of a spot (x=a), and decreases toward the edge of the spot. In this embodiment, laser light intensity is modulated. Accordingly, the laser light intensity is changed with time at x=a as shown in FIG. 3A and at x=b as shown in FIG. 3B. That is, the excitation light is modulated, so the intensity of excitation light is changed in any position in accordance with a cosine function. Here, x=a is a peak position, and x=b is an off-peak position. Thus, excitation light intensity at x=a is higher than excitation light intensity at x=b at any timing.

In general, if the excitation light intensity increases, the fluorescence is saturated. That is, as shown in FIG. 4, if the excitation light intensity is low, the fluorescence light intensity is proportional to the excitation intensity, but if the excitation light intensity increases, the fluorescence light intensity is not proportional to the excitation intensity. This is because the number of excited molecules is limited, and the fluorescence intensity plateaus due to absorption saturation. As described above, even if the excitation light intensity is increased, the fluorescence is not in proportion to the excitation light intensity and is saturated. That is, unless the fluorescence is saturated, the fluorescence intensity is increased in proportion to the excitation light intensity as indicated by the broken line of FIG. 4. In practice, however, saturation occurs at a predetermined excitation light intensity, and the fluorescence intensity plateaus. Incidentally, in this specification, the term "saturation of fluorescence" means that a linear relation between excitation light intensity and fluorescence intensity is lost. That is, saturation of the fluorescence occurs at such excitation light intensity that the solid line deviates from the broken line in FIG. 4. In other words, a saturation range where saturation of fluorescence occurs is a nonlinear range where a relation between laser light intensity and excitation light intensity becomes nonlinear.

Such fluorescence saturation is more likely to occur as the excitation light intensity increases. Further, as the excitation light intensity increases, a saturation degree is high. Accordingly, excitation light having spatial distribution of FIG. 2 is easily saturated near the peak position (x=a), and the maximum fluorescence saturation degree is obtained at the peak position. Further, the excitation light modulated into the cosine function as shown in FIGS. 3A and 3B is easily saturated around peak time ($\omega t = 2n\pi$), and the maximum saturation degree is obtained at the peak time.

In this example, it is assumed that the sample 14 is irradiated with excitation light having intensity enough to induce no saturation of fluorescence at any time with x=b and to induce saturation of fluorescence near the peak position (x=a). Thus, fluorescence having an intensity distribution as indicated by the broken line of FIG. 2 is generated. That is, in FIG. 2, an intensity difference occurs between the excitation light and fluorescence around the peak position (x=a), and the line of excitation light substantially overlaps with the line of fluorescence as a distance from the peak position increases.

Further, the intensity of the fluorescence relative to the modulated excitation light is as indicated by the broken line of FIG. 3A. That is, the excitation light intensity is high at x=a, and fluorescence is saturated. Then, as shown in FIG. 3A, the saturation of fluorescence occurs around peak time ($\omega t = 2n\pi$) and does not occur around midway between peaks ($\omega t = (2n+1)\pi$). That is, in FIG. 3A, an linear relation between the excitation light and fluorescence around the peak time is lost, and the line of excitation light and the line of fluorescence deviate from each other at off-peak time. On the other hand, the excitation light intensity is low at x=b, and no saturation of fluorescence occurs at any time. Thus, the fluorescence intensity is proportional to saturation intensity, and in FIG. 3B, the two lines coincides in form.

The fluorescence intensity is proportional to $1+\cos(\omega t)$ at x=b. On the other hand, the fluorescence intensity is low around peak time at x=a due to saturation of fluorescence and thus is not proportional to $1+\cos(\omega t)$. That is, second order, third-order, . . . harmonic components of the fluorescence intensity appear at x=a. The harmonic components are detected to thereby extract only information of laser light at the spot center. That is, harmonic components include information of laser light at the spot center.

Incidentally, the intensity of non-saturated fluorescence is generally proportional to quantum yield, detection sensitivity of a detection system, absorption cross section, and excitation light intensity. Provided that A represents constant of proportion based on the quantum yield and the detection sensitivity of a detection system, $\sigma$ represents the absorption cross section, C represents a spontaneous emission coefficient, and $B_t$ represents excitation light intensity, the fluorescence intensity $I_f$ is expressed by Numerical Expression 1 in consideration of the saturation of fluorescence.

$$I_f = A \frac{\sigma B_t}{c + 2\sigma B_t} \quad \text{[Numerical Expression 1]}$$

Here, the excitation light is intensity-modulated to a cosine function. Accordingly, $B_t = B(1+\cos(\omega t))$ where B represents the maximum excitation light intensity (amplitude of the excitation light intensity). Thus, the fluorescence intensity $I_f$ is derived from Numerical Expression 2.

$$I_f = A \frac{\sigma B(1+\cos(\omega t))}{c + 2\sigma B(1+\cos(\omega t))} \quad \text{[Numerical Expression 2]}$$

Here, Taylor-expanding Numerical Expression 2 gives Numerical Expression 3.

$$I_f = \sum_{n=1}^{\infty}\left(\frac{-2\sigma B}{c}\right)^n (1+\cos\omega t)^n \quad \text{[Numerical Expression 3]}$$

$$= \sum_{n=1}^{\infty}\left(\frac{-2\sigma B}{c}\right)^n \sum_{k=0}^{n} {_nC_k}\cos^k(\omega t)$$

As described above, $I_f$ is expressed by power series. A term of $\cos(2\omega t)$ is in $(1+\cos(\omega t))^2$, and a term of $\cos(3\omega t)$ is in $(1+\cos(\omega t))^3$. Hence, a term of $(1+\cos(\omega t))^n$, that is, harmonic components of $\cos(n\omega t)$ appear in the fluorescence. As understood from the expression, high-order modulation frequency components are proportional to power series of the amplitude B of excitation light intensity.

Figure 5:
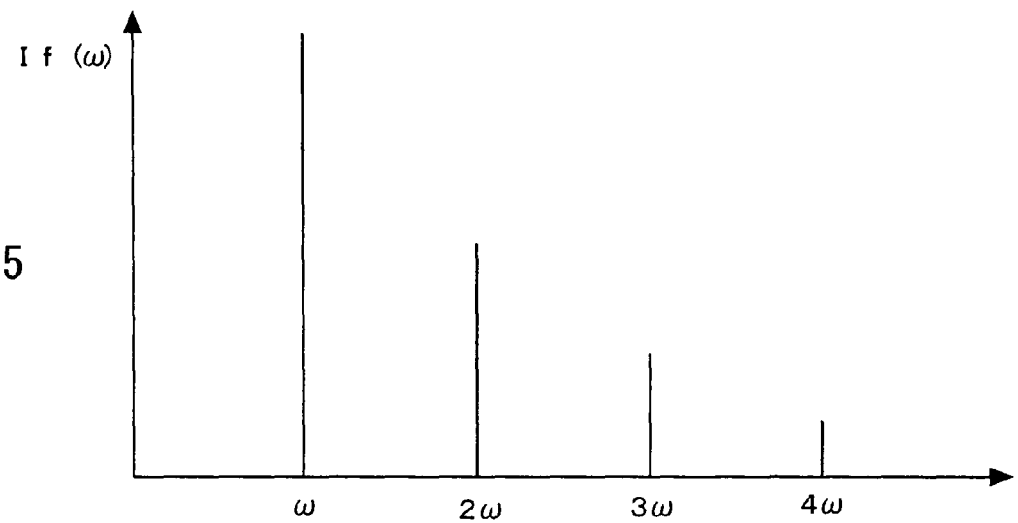
FIG. 5 schematically shows amplitude spectrum relative to angular frequency of fluorescence intensity.

Here, the fluorescence intensity indicated by the broken line of FIG. 3A is Fourier-transformed to determine a spectrum with respect to an angular frequency ω. The determined amplitude spectrum is as shown in FIG. 5. FIG. 5 schematically shows an amplitude spectrum relative to the angular frequency ω of fluorescence. The fluorescence takes a periodic function of Expression 3, so the spectrum is a line spectrum having a peak at a predetermined angular frequency.

As described above, harmonic components appear in the fluorescence, peak values are obtained at ω, 2ω, 3ω, 4ω, . . . . Here, the peak height at the position nω is proportional to $B^n$. For example, a peak in the position ω, is proportional to B, and a peak in the position 2ω is proportional to $B^2$. The larger n is, the lower the peak is. That is, the highest peak appears at the position ω, the second-highest peak appears at the position 2ω, and the third-highest peak appears at the position 3ω.

Figure 6A:
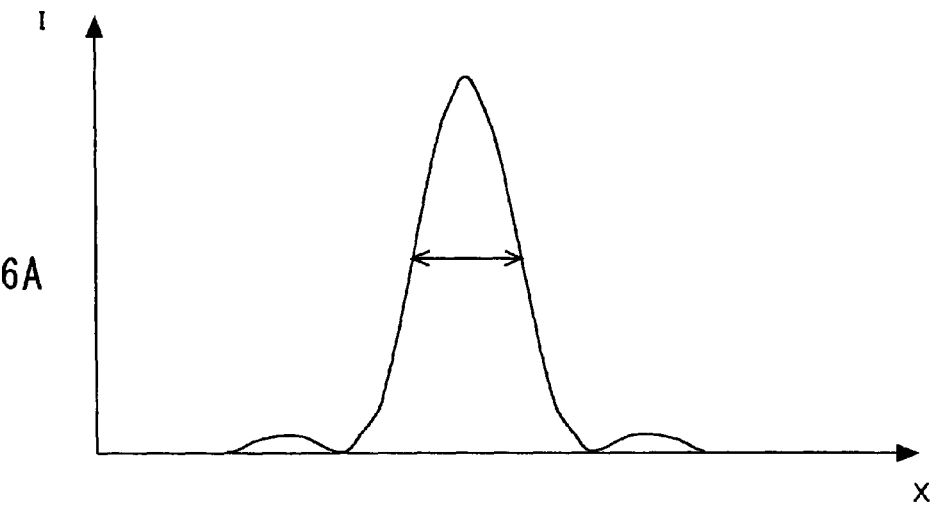
FIG. 6A schematically shows spatial distribution of fluorescence.
Figure 6B:
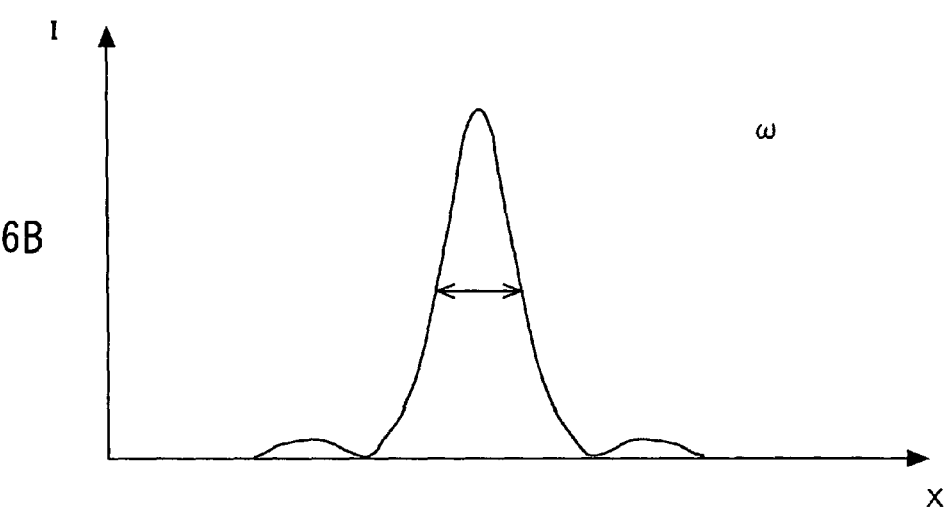
FIG. 6B schematically shows spatial distribution of primary frequency components of fluorescence.
Figure 6C:
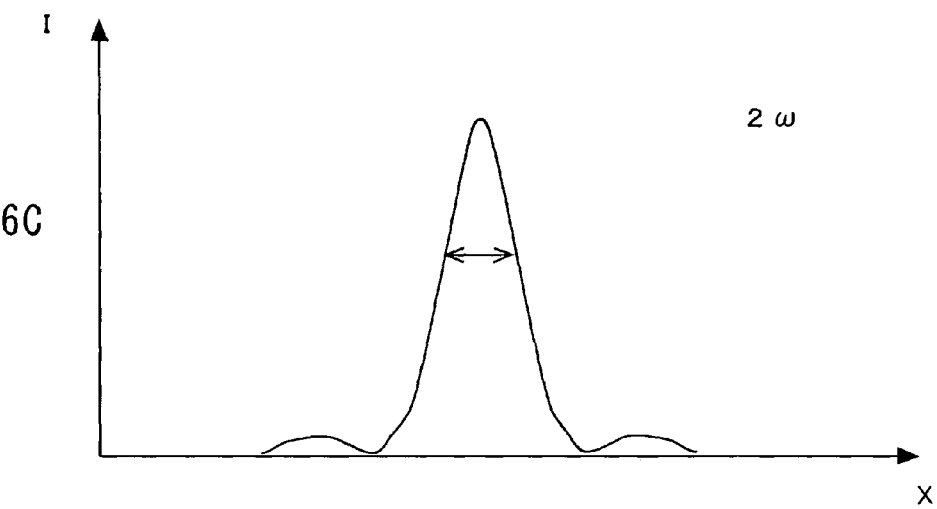
FIG. 6C schematically shows spatial distribution of secondary frequency components of fluorescence.

FIGS. 6A to 6C show spatial distribution of the fluorescence having harmonic components and spatial distribution of the harmonic components. FIG. 6A shows spatial distribution of the fluorescence, which is similar to the spatial distribution as indicated by the broken line of FIG. 2. FIG. 6B shows primary (ω) frequency components of the fluorescence. FIG. 6C shows secondary (2ω)) harmonic components of the fluorescence. FIG. 6B shows. In FIGS. 6A to 6C, the horizontal axis represents a position, and the vertical axis represents fluorescence intensity. Incidentally, the scale of the vertical axis differs among FIGS. 6A to 6C for ease of explanation.

The spatial distribution of FIG. 6B is proportional to B because of primary frequency components. The spatial distribution of FIG. 6C is proportional to $B^2$ because of second-order harmonic components. Accordingly, as shown in FIGS. 6B and 6C, a peak width at half height in spatial distribution of the second-order harmonic components is smaller than that of the primary frequency components. Likewise, spatial resolution of n-order harmonic components is proportional to $B^n$, so a peak width at half height is smaller in higher-order harmonic components. That is, a peak width is smaller and its curve is steeper in higher-order harmonic components. Thus, if higher-order harmonic components are detected, a fluorescence spot is substantially determined by power series of the point spread function, and the spatial resolution can be increased. The spatial resolution can be increased in proportion to the degree of harmonic components to be detected. Incidentally, primary frequency components and all harmonic components are combined and illustrated in FIG. 6A. Further, the spatial distribution of FIG. 6C is based on saturation components of fluorescence. That is, spatial distribution of harmonic components is changed based on the saturation components of fluorescence. That is, intensity of the harmonic components is changed in accordance with intensity of saturation components of fluorescence. In this way, the sample is observed based on saturation components of fluorescence to thereby increase the spatial resolution.

Figure 7:
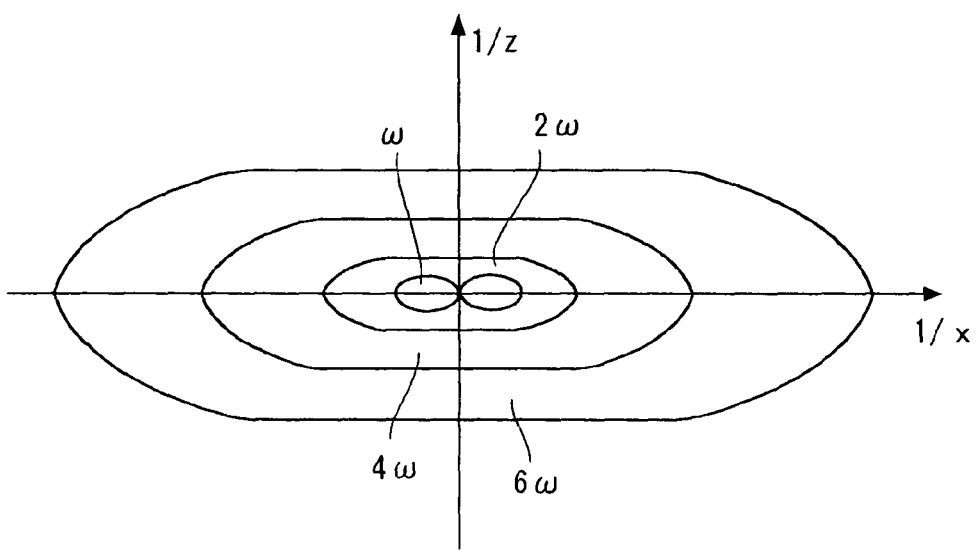
FIG. 7 schematically shows an optical transfer function at the time of detecting high-order frequency components.

FIG. 7 shows an example of an optical transfer function upon detecting high-order frequency components. As shown in FIG. 7, spatial resolution becomes higher in higher-order components. Incidentally, the spatial resolution can be further increased by using a confocal detection method. As described above, this embodiment can increase the spatial resolution in all of the XYZ directions. Incidentally, if a confocal detection method or two-photon fluorescence is used in place of the microscopy method of the present invention, a function substantially similar to an optical transfer function of 2ω is obtained.

For example, second-order harmonic components can be detected with spatial resolution twice as high as the spatial resolution at the time of detecting primary frequency components. In this way, the second- and third-order harmonic components are detected to thereby realize twofold or threefold spatial resolution. Hence, it is possible to detect the components with spatial resolution beyond diffraction limit. The components can be detected with higher resolution than that of the fluorescence microscope of the related art. Needless to say, it is possible to attain n-fold spatial resolution by detecting n-order harmonic components.

As described above, n-order (n is a natural number of 2 or more) harmonic components are extracted and detected to thereby increase spatial resolution. Hence, the lock-in amplifier 23 performs lock-in detection with a predetermined frequency. At this time, a detection frequency of the lock-in amplifier 23 is n times (n is a natural number of 2 or more) as high as the modulation frequency. Further, the components are locked in with a phase where an intensity peak of the excitation light appears and detected. In this way, detection can be performed with high sensitivity, and higher-order harmonic components can be detected. Accordingly, spatial resolution can be further increased. As described above, harmonic components can be extracted with extremely high sensitivity by electrically filtering a frequency band since its frequency is an integral multiple of the modulation frequency of excitation light. Incidentally, harmonics can be detected with a high-pass filter in place of the lock-in detection.

Incidentally, a modulation frequency of the modulator 16 is set much higher than the scanning of the sample 14. That is, the modulation frequency is increased such that plural peaks appear in scanning time of a fluorescence image corresponding to one pixel. For example, if a scanning time for one pixel of the fluorescence image is 1 msec, a modulation frequency is set to 100 kHz. In this case, 100 peaks of excitation light appear in the scamming time of one pixel. The modulation frequency is set higher than the scanning frequency of a sample, so the number of times absorption saturation occurring in the scamming time of one pixel is increased to detect components more precisely.

According to the present invention, as the fluorescence saturation degree increases, the saturation can be easily detected and resolution can be improved. However, if laser light intensity (density) is increased to increase the excitation light intensity, there is a problem that the sample is damaged or fluorescence is faded. In this case, a pulse laser source is preferred as the light source. In this case, for example, a cosine function takes an envelope curve as indicated by the dotted line of FIG. 3, and excitation light has pulse intensity corresponding to the envelope curve. If a pulse laser light source is used, the total irradiation amount can be reduced.

Hence, it is possible to realize the light intensity (density) accomplishing the absorption saturation and prevent the sample from being damaged and the fluorescence from fading. Here, the repetition frequency of the pulse laser light is set much higher than the modulation frequency. That is, the frequencies are determined such that plural pulses appear in one modulation period. For example, if a modulation frequency is 100 kHz, a repetition frequency of 80 MHz can be used. In this case, 800 pulses are included in one period. In this way, precise detection is realized by setting the repetition frequency of the pulse laser light higher than that of the modulation frequency.

Here, if the pulse width is much shorter than a fluorescence life, the fluorescence intensity $I_f$ is expressed by Numerical Expression 4.

$$I_f = A(1-\exp(-\sigma Bt)) \qquad \text{[Numerical Expression 4]}$$

In this example, since $B_t = B(1+\cos(\omega t))$, Taylor-expanding Numerical Expression 4 gives Numerical Expression 5.

$$I_f = A(1 - \exp(-\sigma B(1 + \cos\omega t))) \qquad \text{[Numerical Expression 5]}$$
$$= -\sum_{n=1}^{\infty}\left(\frac{-\sigma B}{n!}\right)^n \sum_{k=0}^{n} nCk\cos^k(\omega t)$$

As for a general pigment, a spontaneous emission coefficient $C \approx 10^8$. Thus, if pulse laser light is used, efficiency is increased.

Further, according to the present invention, it is preferable to use quantum dot as a fluorescence probe. The quantum dot is resistant to fading, and has large absorption cross section. Hence, it is possible to realize the light intensity (density) accomplishing the absorption saturation and easily prevent the sample from being damaged and the fluorescence from being faded. As described above, the present invention is suitable for labeling with a quantum dot. Incidentally, if laser light may be modulated with any periodic function other than the cosine function. Here, the laser light intensity is set to intensity at which saturation of fluorescence occurs at the timing when the maximum laser light intensity is obtained. That is, at the timing at which the maximum laser light is obtained, the sample needs only to be irradiated with laser light in a nonlinear range where the excitation light and fluorescence have a nonlinear relation by occurring the saturation of fluorescence. In FIG. 1, the illustrated fluorescence microscope is an epi-illumination type fluorescence microscope, but the present invention is applicable to a transmitting illumination type fluorescence microscope.

The microscope without the confocal optical system can also realize this embodiment. In this case, the pinhole 21 is removed from the optical setup of FIG. 1. Since the intensity of laser light is low outside of focus position, the saturation of the fluorescence is not observed and the fluorescence response is in the linear range. In this result, the fluorescence out of the focus position will not be detected by demodulation with harmonic frequencies, and the resolution in Z-direction is increased without a confocal optical system. That is, the fluorescence is in the linear range at a point shifting from the focus position in the optical axis direction. Therefore, the saturation of fluorescence dose not occur, it is possible to extract an information from the focus position and its vicinity. In this result, three-dimensional observation becomes possible in a simple configuration without the confocal optical system. Needless to say, the resolution increases further by using the fluorescence microscope with the confocal optical system.

Second Embodiment

A fluorescence microscope of this embodiment has the same structure as that of the first embodiment except that the light source 10 is a pulse laser light source. Target components are observed with two-photon excitation light in a similar fashion to the first embodiment to thereby increase spatial resolution. Incidentally, the same configuration as that of the first embodiment is omitted here.

As the light source 10, for example, a mode-locked titanium sapphire laser (wavelength of 750 nm, a pulse width of 100 fs, and repetition frequency of 80 MHz) is used. Further, the modulator 16 is used to perform intensity-modulation similar to the first embodiment. As the modulator, an electrooptical modulator (EO modulator) is used to perform modulation with 100 kHz. As described in the first embodiment, a repetition frequency of the pulse laser light is set much higher than the modulation frequency.

If two-photon excitation is used, photoexcitation itself is localized in a laser focal point. Therefore, it is unnecessary to consider fluorescent emission except a focal plane, and absorption saturation can be detected with higher sensitivity. That is, two-photon excitation is used not to allow light absorption except in an observation plane. In addition, light scattering efficiency of the two-photon excitation is as low as $\frac{1}{16}$ of that of one-photon excitation, so light intensity can be readily adjusted. As a result, it is possible to prevent light absorption and light scattering before reaching an observation site at the time of observing an inner portion of the sample. Further, similar effects can be attained by a multiphoton excitation method using more than two photons, aside from the two-photon excitation.

Incidentally, the quantum dot may be used as the fluorescence probe as in the first embodiment. If the quantum dot is used, it is possible to easily prevent the sample from being damaged and fluorescence from being faded. Incidentally, the present invention is applicable to a fluorescence microscope other than the confocal type microscope. Further, the fluorescence microscope of the present invention may be used as a general fluorescence microscope except functions of the intensity modulation and lock-in detection. Hence, it is possible to easily switch high-resolution detection and general detection.

Third Embodiment

A fluorescence microscope of this embodiment applies laser beams of different intensities to observe a target site without modulating the laser light. The basic structure of the fluorescence microscope of this embodiment has the same structure as that of the fluorescence microscope of the first embodiment, so its description is omitted here. The fluorescence microscope of this embodiment is not provided with the modulator 16 in the fluorescence microscope of FIG. 1. Then, the sample 14 is irradiated with laser beams of different intensities from the light source 10. At this time, to irradiate the sample 14 with laser beams of different intensities, an output power of the light source 10 may be changed, or an intensity level of the laser light may be changed by using a filter such as an ND filter. Further, two or more light sources may be used. Further, these sources may be used in combination to change an intensity level of the laser light. Incidentally, laser beams of different intensities have substantially the same wavelength.

Here, the different intensities of the laser light are referred to as "first intensity" and "second intensity". That is, the laser light from the light source 10 is applied to the sample 14 at the first intensity and the second intensity. Needless to say, the sample 14 may be irradiated with laser light at intensity other than the first intensity and second intensity. It is also possible to apply the laser light to the sample 14 with 3 or more different intensities. Here, the first intensity is higher than the second intensity. The first intensity should be high enough to cause saturation of fluorescence. That is, at the first intensity, the sample is irradiated with laser light in a nonlinear range where the excitation light and fluorescence have a nonlinear relation. Needless to say, the second intensity may cause saturation of fluorescence. If the sample 14 is irradiated with laser light from the light source 10 as excitation light at the first intensity, fluorescence from the sample 14 is saturated. In this case, as shown in FIG. 4, the first intensity is set to such excitation light intensity that the excitation light and fluorescence are not proportional to each other. In other words, the first intensity corresponds to a nonlinear range where the excitation light and fluorescence have a nonlinear relation. Here, the first intensity is set to $B_1$, and the second intensity is set to $B_2$. Then, the sample 14 is scanned with laser light at the first intensity $B_1$ and the second intensity $B_2$. For example, all or part of the sample 14 is scanned with laser light at the first intensity $B_1$ and then at the second intensity $B_2$. Needless to say, the sample may be scanned in reverse order. As a result, a fluorescence image can be captured at the first intensity $B_1$ and the second intensity $B_2$. That is, a fluorescence image captured at the first intensity $B_1$ and a fluorescence image captured at the second intensity $B_2$ can be provided. Here, the fluorescence of at least the first intensity $B_1$ includes the saturation components of fluorescence.

Next, a method of analytically deriving the saturation components of fluorescence is described. To be specific, based on fluorescence intensities corresponding to the first intensity $B_1$ and second intensity $B_2$ at the same portion of the sample 14, the saturation components of fluorescence at this portion are derived. To describe a particular point of the scanned portion, the fluorescence intensity corresponding to the first intensity $B_1$ is $I_{f1}$, and the fluorescence intensity corresponding to the second intensity $B_2$ is $I_{f2}$. Accordingly, in a graph where the horizontal axis represents excitation light intensity, and the vertical axis represents fluorescence intensity as shown in FIG. 4, detection results are plotted to coordinates $(B_1, I_{f1})$ and $(B_2, I_{f2})$. Further, if the excitation light intensity is 0, the fluorescence intensity is 0. Hence, the horizontal axis representing excitation light there are three points $(0, 0)$, $(B_1, I_{f1})$, and $(B_2, I_{f2})$ in a graph with intensity and the vertical axis representing fluorescence intensity. The saturation components of fluorescence are derived based on the three points. To be specific, fitting quadratic function to the above three points gives $I_f = pB^2 + qB + r$. The value $I_f$ expressed by the quadratic function is approximate to the function as indicated by the solid line of, for example, FIG. 4. Incidentally, $I_f$ is fluorescence intensity, B is excitation light intensity, and p and q are coefficients derived from the fitting. Incidentally, if the excitation light intensity is 0, the fluorescence intensity is 0, r is ideally 0.

Here, a component of the 1st power of B in $I_f$, that is, qB is a component where the fluorescence is proportional to the excitation light. To be specific, qB is indicated by the broken line of FIG. 4. Further, the 2nd power of B in $I_f$, that is, $pB^2$ represents the saturation components of fluorescence. To be specific, $pB^2$ represents a difference between the broken line of FIG. 4 and the solid line representing the actual fluorescence intensity. Strictly speaking, $pB^2$ is based on the difference between the broken line of FIG. 4 and the solid line representing the actual fluorescence intensity. That is, the difference between the broken line of FIG. 4 and the solid line representing the actual fluorescence intensity includes a term having three or more degrees. Here, since at least the first intensity $B_1$ causes saturation of fluorescence, $p \neq 0$.

In the case of scanning the sample in XYZ directions, calculated coefficients are functions of (x, y, z). That is, a secondary coefficient p indicates spatial distribution of intensity of the saturation components of fluorescence. Thus, an image of the saturation components of fluorescence is represented by p (x, y, z). That is, an image of the saturation components of fluorescence is formed by the coefficient p of a quadratic term of the fit quadratic function. In this example, an image of the saturation components of fluorescence shows spatial distribution of intensity of the saturation components of fluorescence in the case of scanning the sample 14 with light. An image of the saturation components of fluorescence can be captured in this way. An image of the saturation components of fluorescence is observed with increased spatial resolution. The observation can be made with twofold spatial resolution if the coefficient of the quadratic term is used.

Incidentally, in the above description, fluorescence is detected only at the first intensity and the second intensity, but fluorescence may be detected with 3 or more laser light intensities. For example, in the case of detecting the fluorescence with 3 or more laser light intensities, it is possible to fit a cubic function. In this case, a quadratic or cubic term represents the saturation components of fluorescence. Considering the cubic term, spatial resolution can be further increased. In this case, spatial resolution can be increased threefold in consideration of the coefficient of the cubic term.

The fluorescence is detected with n laser light intensities, making it possible to fit the n-order function. Then, spatial resolution can be further increased by using a higher-order term. Therefore, if a coefficient of the polynomial is used, spatial resolution can be increased in proportion to the degree of the polynomial. To be specific, n-fold spatial resolution can be obtained when the fluorescence is detected with n laser light intensities. Incidentally, in this case, the sum of two or more terms represents the saturation components of fluorescence. It is preferred to detect a target component with laser beams of different intensities more than n for more precise detection.

Incidentally, in this embodiment, scanning is performed with the constant laser light intensity, but the present invention is not limited thereto. For example, scanning may be performed with varying laser light intensities. In this case as well, fluorescence is detected with 2 or more different intensities, and it is possible to fit the quadratic function to a fluorescence change based on the excitation light. Therefore, the sample 14 can be observed based on the saturation components of fluorescence. As described above, in this embodiment, laser light is applied with at least two intensities corresponding to positions on the sample 14. Then, fitting a function with two or more degrees gives coefficients of the term with two or more degrees. The spatial distribution of the coefficients is an image of the saturation components of fluorescence. Hence, the sample 14 can be observed based on the saturation components of fluorescence.

In this embodiment, scanning should be performed twice at different intensities, but a modulator or lock-in amplifier can be omitted, and thus the structure can be more simplified as compared with the first embodiment.

As described above, the present invention centers on the point that fluorescence is saturated if excitation light intensity increases. The fluorescence is observed based on the saturation components of fluorescence, and spatial resolution can be increased. In this way, the spatial resolution is increased, so even if fluorescent materials exist close to each other in the sample 14, the materials can be separated and observed.

INDUSTRIAL APPLICABILITY

The present invention can increase spatial resolution can be increased and thus is applicable to various fields such as medical and biological researches.

The invention claimed is:

1. A fluorescence microscope, comprising:
   a laser light source emitting laser light as excitation light;
   an objective lens focusing the laser light and applying the focused laser light to a sample;
   a detector detecting fluorescence generated in the sample with the laser light; and
   a scanning unit scanning the sample while moving the sample relative to the laser light,
   wherein the laser light is applied to the sample with varying intensities to be in a nonlinear range at a maximum intensity, a saturation of fluorescence occurring in the nonlinear range such that an intensity of the laser light and an intensity of fluorescence have a nonlinear relation, and
   the fluorescence corresponding the intensity of the laser light is detected with the detector, and the sample is observed based on the saturation components of fluorescence.

2. The fluorescence microscope according to claim 1, further comprising:
   a modulator modulating the intensity of the laser light such that the intensity is changed with time,
   wherein the sample is irradiated with intensity to be in the nonlinear range at a time when the intensity of the laser light peaks;
   the sample is scanned under modulation with the modulator, and fluorescence generated in the sample is detected with the detector; and
   harmonic components corresponding to a frequency of the modulator are extracted from the fluorescence detected with the detector to observe.

3. The fluorescence microscope according to claim 2, wherein the harmonic components are extracted with a lock-in amplifier.

4. The fluorescence microscope according to claim 1, wherein a pulse laser light source is used as the laser light source.

5. The fluorescence microscope according to claim 1, wherein the laser light is applied to the sample at least two intensities of a first intensity being in the nonlinear range and a second intensity different from the first intensity, and
   scanning is performed under such a condition that the laser light is applied to the sample with each of the first and second intensity, and the saturation components of fluorescence from the sample are derived based on fluorescence intensity at the first intensity and fluorescence intensity at the second intensity.

6. The fluorescence microscope according to claim 1, wherein the laser light source is a multiphoton excitation light source that generates multiphoton excitation.

7. The fluorescence microscope according to claim 1, further comprising:
   a separating unit separating fluorescence from the laser light based on a wavelength difference,
   wherein the fluorescence separated with the separating unit is detected with the detector.

8. The fluorescence microscope according to claim 1, further comprising:
   a focus position changing unit changing a focus position of the objective lens along an optical axis.

9. The fluorescence microscope according to claim 1, wherein the fluorescence generated by applying the laser light to the sample is detected with the detector through a confocal optical system.

10. A fluorescence microscopy method for irradiating a sample with laser light as excitation light to detect fluorescence from the sample to observe the sample, comprising:
    focusing the laser light and applying the focused laser light to a sample;
    changing intensity of the laser light to be in a nonlinear range at a maximum intensity, saturation of fluorescence occurring in the nonlinear range such that the intensity of the laser light and intensity of fluorescence have a nonlinear relation;
    scanning the sample while moving the sample relative to the laser light;
    separating the laser light and fluorescence generated in the sample and derived from the laser light;
    detecting the fluorescence separated from the laser light; and
    observing the sample based on saturation components of fluorescence with the detected fluorescence.

11. The fluorescence microscopy method according to claim 10, further comprising:
    modulating intensity of the laser light such that the intensity is changed with time;
    focusing laser light and applying the laser light to the sample to be in the nonlinear range at a time when the modulated laser light peaks; and
    scanning the sample while moving the sample relative to the laser light under modulation with the modulator.

12. The fluorescence microscopy method according to claim 11, wherein harmonic components corresponding to a modulation frequency are extracted from the detected fluorescence to observe.

13. The fluorescence microscopy method according to claim 10, wherein the laser light is a pulse laser light, and the pulse laser light is intensity-modulated.

14. The fluorescence microscopy method according to claim 10, wherein the laser light is applied to the sample at least two intensities of a first intensity being in the nonlinear range and a second intensity different from the first intensity, and
    scanning is performed with each of the first and second intensity; and
    saturation components of fluorescence are derived based on fluorescence intensity at the first intensity and fluorescence intensity at the second intensity.

15. The fluorescence microscopy method according to claim 10, wherein fluorescence is detected by a multiphoton excitation method.

16. The fluorescence microscopy method according to claim 10, wherein the sample is labeled with a quantum dot.

17. The fluorescence microscopy method according to claim 10, wherein a focus position of the laser light in the sample changes along an optical axis to detect the fluorescence.

18. The fluorescence microscopy method according to claim 10, wherein the fluorescence generated by applying the laser light to the sample is detected through a confocal optical system.

19. A fluorescence microscope, comprising:
a laser light source emitting laser light as excitation light;
an objective lens focusing the laser light and applying the focused laser light to a sample;
a detector detecting fluorescence generated in the sample with the laser light; and
a scanning unit scanning the sample while moving the sample relative to the laser light,
wherein the laser light is applied to the sample with varying intensities such that saturation of fluorescence occurs at a maximum intensity of the laser light, and
the fluorescence corresponding to the intensity of the laser light is detected with the detector, and the sample is observed based on saturation components of fluorescence.

* * * * *